(12) United States Patent
Wågdahl

(10) Patent No.: US 10,166,153 B2
(45) Date of Patent: Jan. 1, 2019

(54) PANT-TYPE ABSORBENT ARTICLE

(71) Applicant: SCA Hygiene Products AB, Göteborg (SE)

(72) Inventor: Inge Wågdahl, Göteborg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 15/547,671

(22) PCT Filed: Feb. 9, 2015

(86) PCT No.: PCT/SE2015/050140
§ 371 (c)(1),
(2) Date: Jul. 31, 2017

(87) PCT Pub. No.: WO2016/130049
PCT Pub. Date: Aug. 18, 2016

(65) Prior Publication Data
US 2018/0021186 A1 Jan. 25, 2018

(51) Int. Cl.
*A61F 13/15* (2006.01)
*A61F 13/496* (2006.01)
(Continued)

(52) U.S. Cl.
CPC .... *A61F 13/4963* (2013.01); *A61F 13/15203* (2013.01); *A61F 13/49015* (2013.01);
(Continued)

(58) Field of Classification Search
CPC ............ A61F 13/4963; A61F 13/15203; A61F 13/49015; A61F 13/51464;
(Continued)

(56) References Cited

U.S. PATENT DOCUMENTS 5,236,430 A  8/1993  Bridges
5,246,433 A  9/1993  Hasse et al.
(Continued)

FOREIGN PATENT DOCUMENTS

WO  WO 2005/122985 A1  12/2005
WO  2006-038837 A1  4/2006
(Continued)

OTHER PUBLICATIONS

International Search Report (PCT/ISA/210) dated Sep. 28, 0015, by the European Patent Office as the International Searching Authority for International Application No. PCT/SE2015/050140.
(Continued)

*Primary Examiner* — Jacqueline Stephens
(74) *Attorney, Agent, or Firm* — Buchanan Ingersoll & Rooney PC

(57) ABSTRACT

A pant-type absorbent article, such as a pant diaper, a sanitary pant or incontinence pant, includes a front portion, a back portion and a crotch portion, wherein lateral side portions of the front portion and back portion are superposed so that their inner surfaces face each other and being joined to each other along side seams. At least part of said front and back portions comprises an elastic laminate including first and second fibrous layers and an elastic film layer located therebetween, the first fibrous layer forms an inner wearer-facing side of the elastic laminate having a basis weight of between 13 and 30 g/m² and the basis weight of the first fibrous layer is between 10 and 300% higher than the basis weight of the second fibrous layer, and wherein the first fibrous layers face each other along said side seams.

12 Claims, 2 Drawing Sheets

US 10,166,153 B2
Page 2

(51) Int. Cl.
| | |
|---|---|
| *D21H 27/36* | (2006.01) |
| *A61F 13/514* | (2006.01) |
| *B32B 5/02* | (2006.01) |
| *B32B 5/06* | (2006.01) |
| *B32B 5/08* | (2006.01) |
| *B32B 7/04* | (2006.01) |
| *B32B 7/14* | (2006.01) |
| *B32B 27/12* | (2006.01) |
| *B32B 27/20* | (2006.01) |
| *B32B 27/30* | (2006.01) |
| *B32B 27/32* | (2006.01) |
| *B32B 3/26* | (2006.01) |
| *A61F 13/49* | (2006.01) |
| *B32B 25/10* | (2006.01) |
| *B32B 27/40* | (2006.01) |
| *D21H 13/14* | (2006.01) |

(52) U.S. Cl.
CPC ........ *A61F 13/51464* (2013.01); *B32B 3/266* (2013.01); *B32B 5/022* (2013.01); *B32B 5/06* (2013.01); *B32B 5/08* (2013.01); *B32B 7/045* (2013.01); *B32B 7/14* (2013.01); *B32B 25/10* (2013.01); *B32B 27/12* (2013.01); *B32B 27/205* (2013.01); *B32B 27/302* (2013.01); *B32B 27/32* (2013.01); *B32B 27/325* (2013.01); *B32B 27/40* (2013.01); *D21H 13/14* (2013.01); *D21H 27/36* (2013.01); *A61F 13/15739* (2013.01); *A61F 2013/15406* (2013.01); *B32B 2262/0253* (2013.01); *B32B 2262/0276* (2013.01); *B32B 2262/062* (2013.01); *B32B 2262/14* (2013.01); *B32B 2274/00* (2013.01); *B32B 2307/51* (2013.01); *B32B 2307/581* (2013.01); *B32B 2307/718* (2013.01); *B32B 2307/724* (2013.01); *B32B 2307/726* (2013.01); *B32B 2555/02* (2013.01)

(58) Field of Classification Search
CPC ..... A61F 13/15739; A61F 2013/15406; B32B 3/266; B32B 5/022; B32B 5/06; B32B 5/08; B32B 7/045; B32B 7/14; B32B 25/10; B32B 27/12; B32B 27/205; B32B 27/302; B32B 27/32; B32B 27/325; B32B 27/40
USPC ... 604/396, 394, 392, 385.3, 385.24, 385.29
See application file for complete search history.

(56) References Cited

U.S. PATENT DOCUMENTS

| | | | |
|---|---|---|---|
| 5,769,838 A | 6/1998 | Buell et al. | |
| 8,641,695 B2 | 2/2014 | Edwall et al. | |
| 2004/0182499 A1* | 9/2004 | Collier, IV | A61F 13/4902 156/164 |
| 2007/0293833 A1* | 12/2007 | Wennerback | A61F 13/15203 604/385.01 |
| 2008/0009817 A1* | 1/2008 | Norrby | A61F 13/15593 604/385.3 |
| 2009/0107614 A1 | 4/2009 | Cartier et al. | |
| 2010/0168704 A1 | 7/2010 | Thomas et al. | |
| 2010/0262109 A1* | 10/2010 | Eriksson | A61F 13/49011 604/385.3 |
| 2014/0255658 A1 | 9/2014 | Muslet et al. | |
| 2015/0080820 A1 | 3/2015 | Fjeldsa | |

FOREIGN PATENT DOCUMENTS

| | | |
|---|---|---|
| WO | WO 2007/008128 A1 | 1/2007 |
| WO | WO 2007/094706 A1 | 8/2007 |
| WO | WO 2007/138373 A1 | 12/2007 |
| WO | 2008/060194 A1 | 5/2008 |
| WO | 2008/060205 A1 | 5/2008 |
| WO | WO 2013/167170 A1 | 11/2013 |

OTHER PUBLICATIONS

Written Opinion (PCT/ISA/237) dated Sep. 28, 2015, by the European Patent Office as the International Searching Authority for International Application No. PCT/SE2015/050140.
International Preliminary Report on Patentability (PCT/IPEA/409) dated Jan. 20, 2017, by the European Patent Office as the International Searching Authority for International Application No. PCT/SE2015/050140.
Letter to the European Patent Office from Valea AB dated Nov. 2, 2015, for International Application No. PCT/SE2015/050140.
Office Action (Examination Report No. 1 for Standard Patent Application) dated Aug. 18, 2017, by the Australian Patent Office in corresponding Australian Patent Application No. 2015382479. (4 pages).
The extended European search report dated Jun. 25, 2018, by the European Patent Office in corresponding European Patent Application No. 15882183.5. (8 pages).
Office Action dated Sep. 11, 2018 by the Mexican Institute of Industrial Property in corresponding Mexican Patent Application No. MX/a/2017/010209 and an English translation of the Office Action. (11 pages).

* cited by examiner

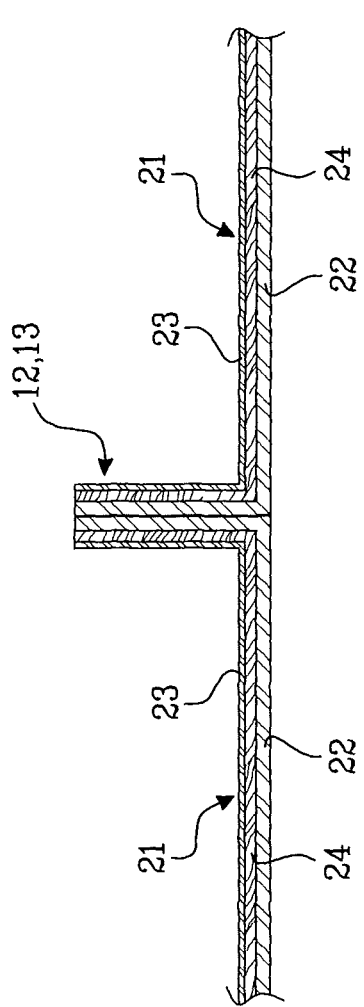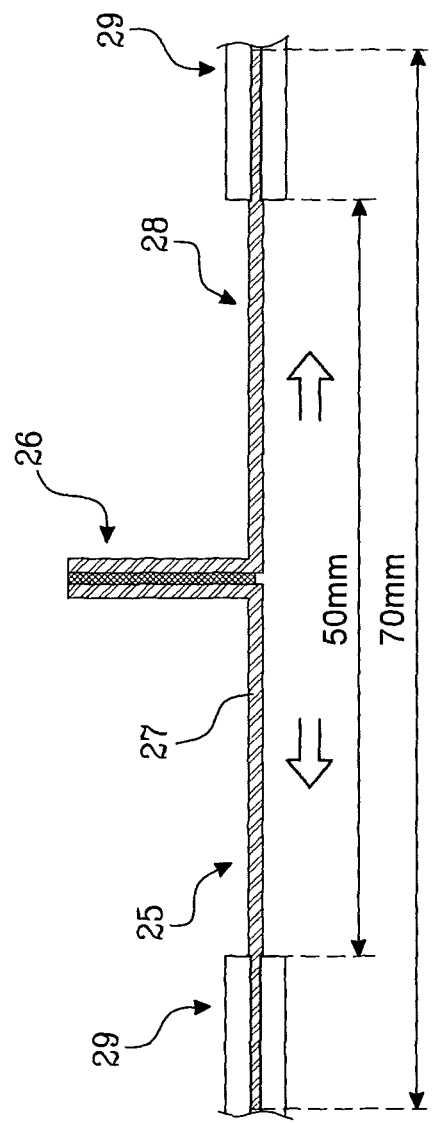

PANT-TYPE ABSORBENT ARTICLE

TECHNICAL FIELD

The present disclosure refers to pant-type absorbent article, such as a pant diaper, a sanitary pant or incontinence pant. The article comprises a front portion, a back portion and a crotch portion, wherein lateral side portions of the front portion and back portion are superposed so that their inner surfaces face each other and being joined to each other along side seams to define a waist opening and a pair of leg openings. At least part of, including said lateral side portions, of said front and back portion comprises an elastic laminate, said elastic laminate comprising first and second fibrous layers and an elastic film layer located there between

BACKGROUND

Pant-type absorbent articles resemble ordinary underwear and include a pant-shaped chassis and an absorbent core component integrated with the chassis. They are intended to fit comfortably and snugly about the wearer. It is further desirable that the articles are capable of being pulled up and down over the hips of the wearer to allow the wearer or caregiver to easily put on and remove the article when it has been soiled. There is also a requirement that they should be soft and textile-like.

Pant-type absorbent articles, in which portions of the chassis are composed of an elastic laminate comprising first and second layers of fibrous material and an elastic film layer located there between, are known through for example WO 2005/122985. Such pant-type articles are smooth and discrete to wear.

Since such articles are disposable products, the cost aspect is very important. For cost reasons, the material layers included in the article must be as thin as possible. At the same time, quality and strength requirements must be fulfilled. More particularly, such articles must combine properties of comfort and good fit for the user with strength, such that the article is comfortable and discrete to wear, yet its integrity must be maintained when it is put on and during use. The pant article is exposed to considerable stresses especially when being put on. Those regions which are most subject to stress and where failure is most likely to occur, are those regions in which the components of the article are joined together, i.e. the seams of the article and especially the side seams joining the front at back portions. These side seams are commonly formed by ultrasonic welding, thermobonding or gluing or a combination thereof. The pant article is stretched when being pulled over the user's hips, wherein the side seams are exposed to great stresses. Pant-type absorbent articles having front and back portions of elastic laminate, wherein the side seams are formed by bonding two elastic laminates together often have an insufficient bond strength for the stresses occurring during use of the article. The problem has been accentuated as the trend is going to thinner and softer elastic laminates. The side seams may either be formed by superposing the inner surfaces of the lateral edge portions of the front and back portions, wherein the side seams will protrude from the plane of the elastic laminate or alternatively by joining the inner surface of one lateral edge portion to the outer surface of the other lateral portion in an overlapping manner, wherein the side seams will be in the same plane as the elastic laminate.

WO 2007/138373 discloses a pant-type absorbent article comprising an elastic laminate and wherein the weld seams are reinforced by reinforcing strips of nonwoven material applied on the inner surface of the elastic laminate.

WO 2007/094706 discloses a pant-type absorbent article comprising an elastic laminate and wherein the weld seams are reinforced by spraying fibers in a softened state onto at least one of the web materials in the seam prior to bonding.

WO 2013/167170 discloses reinforcing the side seams in a pant-type absorbent article comprising an elastic laminate by folding a nonwoven layer of the lateral side portions upon itself in the area of the side seam to provide an additional layer in the side seam.

SUMMARY

It is an object of the disclosure to provide a pant-type absorbent article comprising an elastic laminate, which can be manufactured in an easy and cost effective manner while providing the desired strength properties and soft textile feel. The disclosure refers to a pant-type absorbent article of the kind referred to in the introduction and wherein the first fibrous layer of the elastic laminate forming the inner wearer-facing side of the elastic laminate has a basis weight of between 13 and 30 g/m$^2$ and wherein the basis weight of the first fibrous layer is between 10 and 300% higher than the basis weight of the second fibrous layer of the elastic laminate, wherein the first fibrous layers face each other along said side seams.

The basis weight of the first and second fibrous layers refers to the basis weight of the original fibrous materials used for producing the elastic laminate and not to the basis weight that the fibrous layers may have in the elastic laminate, after having been exerted to bonding to the elastic film and other process steps during the production of the elastic laminate.

The side seams may be provided by ultrasonic welding, thermal bonding, glue or by combinations thereof.

The first and second fibrous layers may be nonwoven material selected from the following group: spunbond, meltblown, mixtures thereof, carded, hydroentangled.

The first and second fibrous layers may be of the same type of fibrous material and differ only by their basis weight.

The elastic laminate may extend transversely across the width of the front portion as well as transversely across the width of the back portion.

The first fibrous layer of said elastic laminate forming the inner wearer-facing side of the elastic laminate may have a basis weight of at least 15 g/m$^2$, preferably at least 18 g/m$^2$.

The basis weight of the first fibrous layer may be at least 20%, preferably at least 25% higher than the basis weight of the second fibrous layer of the elastic laminate.

The basis weight of the first fibrous layer may be not more than 200% higher than the basis weight of the second fibrous layer of the elastic laminate.

The elastic laminate may be a stretch-bonded laminate

BRIEF DESCRIPTION OF THE DRAWINGS

Embodiments of the invention will below be described in greater detail with reference to the accompanying drawings.

FIG. 2 is a cross section through a side seam according to an embodiment of the invention.

FIG. 3 is a schematic view of a test procedure for testing the sealing strength of a seam joining together two web materials.

DETAILED DESCRIPTION OF PREFERRED EMBODIMENTS

Figure 1:
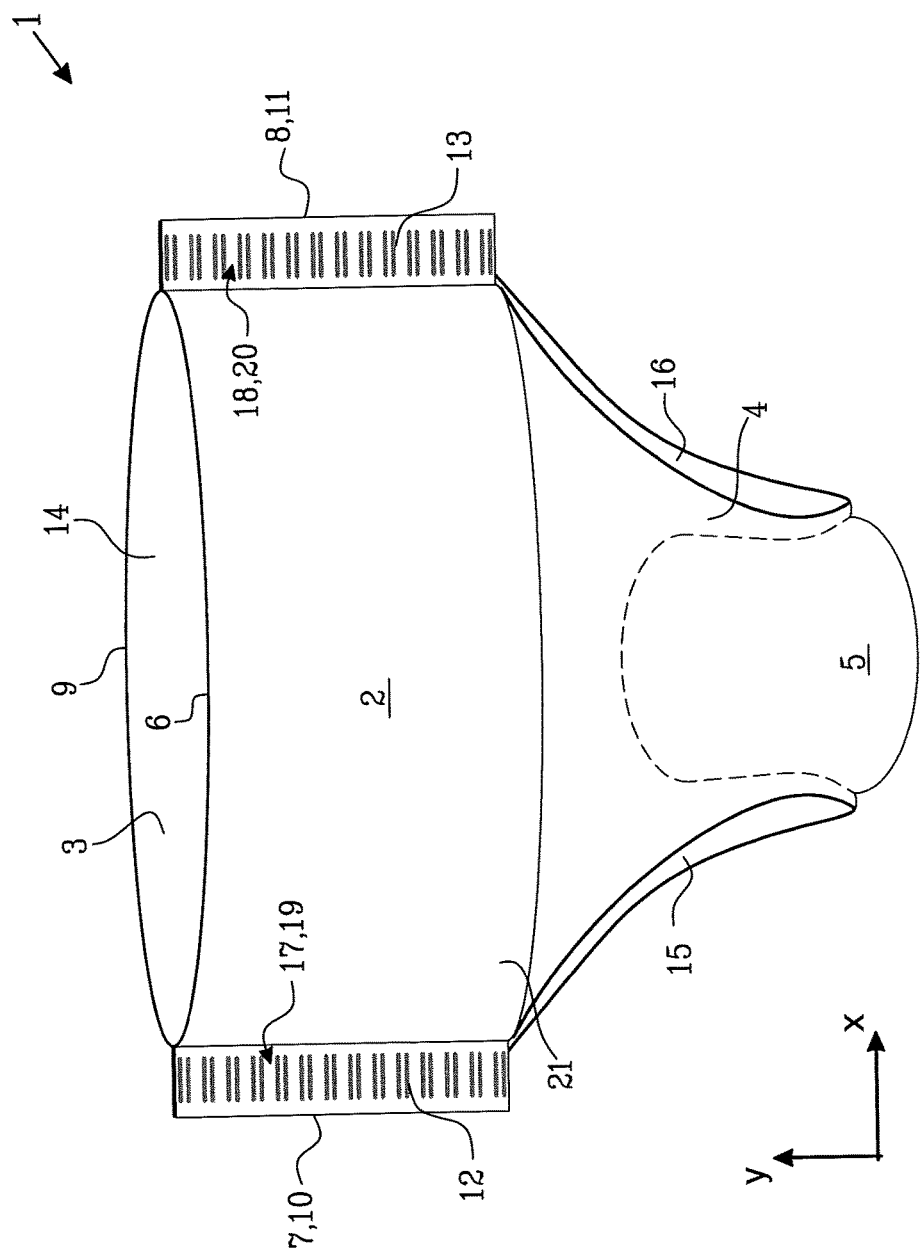
FIG. 1 is a schematic perspective view of an illustrative embodiment of a pant-type article.

FIG. 1 shows a pant-type absorbent article intended to enclose the lower part of the wearer's trunk like a pair of underwear. The disclosure mainly refers to disposable absorbent articles, which means articles that are not intended to be laundered or otherwise restored or reused as an absorbent article after use. The disclosure refers to pant-type absorbent articles such as a pant diapers, sanitary pants and incontinence pants.

The pants 1 have a transverse and a longitudinal direction, x and y, and comprises a front portion 2, a back portion 3 and a crotch portion 4 located there between as seen in the longitudinal direction y. An absorbent core 5 is located at least in the crotch portion 4 and may extend into the front and/or back portions 2 and 3. A liquid impervious backsheet (not shown) underlies the absorbent core 5 on the garment facing side.

The front portion 2 has a front transverse edge 6 and first and second longitudinal side edges 7 and 8. The back portion 3 has a back transverse end edge 9 and first and second longitudinal side edges 10 and 11. The front and back portions 2 and 3 are joined to each other along their respective first and second longitudinal side edges by ultrasonic welds, thermobonding, glue strings or the like to form first and second side seams 12 and 13 and to define a waist-opening 14 and first and second leg openings 15 and 16. The areas of the front and back portions 2 and 3 adjacent the respective longitudinal side edges 7, 8, 10 and 11 that form the side seams 12 and 13 are referred to as lateral side portions 17, 18, 19 and 20.

The lateral side portions 17, 18 of the front portion 2 are superposed with the respective lateral side portions 19, 20 of the back portion 3 in a manner that their inner surfaces face each other, wherein side seams are formed 12, 13 which are of a type that protrudes from the plane of the front and back portions 2 and 3.

The pants may further comprise an elastic waist band (not shown) secured to the transverse end edges 6 and 9 of the front and back portions 2 and 3.

The pants comprises an outer cover which in at least part of the front and back portions 2 and 3 including the lateral side portions 17, 18, 19 and 20 is elastic and comprises an elastic laminate 21. The elastic laminate 21 comprises first and second fibrous layers 22, 23 and an elastic film layer 24 located there between. The elastic laminate 21 may also comprise one or more additional fibrous layers laminated to one or both of the first and second fibrous layers. Such additional fibrous layers may be present only in parts of the elastic laminate 21. Thus the elastic laminate 21 need not be identical all over its area, but may comprise different layers in different areas.

By the term "elastic" is meant that the material is capable of being extended under a force and then is capable of contracting back to or towards its initial length once the force is removed. For the purpose of the present invention an "elastic" material should have an elasticity in at least one direction of at least 30% as measured by the Elasticity test specified herein. The elastic laminate 21 used in the pant-type absorbent article according to the invention should have elasticity in the x-direction of the article of at least 30%, preferably at least 50%, more preferably at least 70%, as measured by the Elasticity test specified herein.

Preferably the elastic laminate material 21 is also elastic in the y-direction of the article. However the elasticity in the y-direction is preferably lower than in the x-direction.

The term "non-elastic" refers to any material that does not fall within the definition of an "elastic" material given above.

The elastic laminate 21 may cover the entire article, including the crotch portion 4 and the entire front and back portions 2 and 3. However in a preferred embodiment a substantial part of or the entire crotch portion 4 of the article is free from the elastic laminate material 21, wherein a substantially inelastic crotch panel material is arranged in the crotch portion.

The elastic laminate 21 preferably extends laterally across the width of the front portion 2 between the first and second side edges 7 and 8 as well as laterally across the width of the back portion 3 between the first and second side edges 10 and 11.

It is advantageous that the outer fibrous layers are chosen so that they, in combination with the inner elastic film layer, give the material high resistance to puncture. They also provide a soft and cloth-like feel to the laminate. Examples of suitable materials are carded webs, hydroentangled materials, spunbond materials meltblown materials, spunbond-meltblown-spunbond (SMS) materials, spunbond-meltblown (SM) materials and the like. The basis weight of the fibrous material layers will be discussed below. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

At least one of the fibrous layers of the elastic laminate may be a creped nonwoven material. The creped nonwoven will increase the puncture resistance of the laminate puncture resistant and allow it to be subjected to the pulling and stretching forces that occur when putting on and taking off the pant article without breaking and tearing.

The middle layer is preferably a breathable elastic film 24, such as porous, monolithic, apertured, punctured etc., having a basis weight between 20 and 80 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 100 g/m$^2$ or less, more preferably no more than 90 g/m$^2$.

In one embodiment the first and second layers of fibrous material have been bonded to the elastic film layer while this is in a stretched state, so called stretch-bonding. The bonding will be by adhesive, ultrasonic welding or the like. The resulting laminate will be elastically stretchable.

WO 2012/036599 discloses a stretch-bonded elastic laminate wherein at least one nonwoven layer is bonded to an elastic film layer in a bonding pattern comprising a plurality of bonding elements. The elastic film layer is stretched during bonding. Apertures are formed in the film layer close to at least some of the bonding elements.

WO 2012/036600 is another example of a stretch-bonded elastic laminate comprising at least one nonwoven layer bonded to an elastic film layer in a bonding pattern, while the elastic film is held in a stretched condition.

WO 2010/104429 discloses a further example of a stretch-bonded elastic laminate wherein the elastic film is heated and stretched during lamination to at least one nonwoven layer.

WO 2013/002691 discloses stretch-bonding of an elastic laminate wherein the elastic film is stretched in at least two stretching steps before laminating it to at least two nonwoven webs, The elastic laminate material 21 is preferably arranged as an outside coversheet material as well as inner coversheet material over at least part of the front portion 2 and back portion 3. The elastic laminate material may constitute the sole component of the front and back portions in at least 20%, preferably at least 25%, more preferably at least 30% and most preferably at least 40% of the total surface area of the article.

A more detailed description of examples of pant-type diapers comprising an elastic laminate can be found in WO 2005/122985, which accordingly is incorporated herein in its entirety to the extent that the description therein is not inconsistent with the description herein.

The bonds between elastic laminate materials 21, such as in the side seams 12 and 13, may sometimes be insufficient, especially for thin laminates. The side seams 12 and 13 are exerted to considerable stress when the pants are being pulled on over the hips of the wearer and also during use of the article. The bonds in these side seams are normally accomplished by ultrasonic welding or thermobonding, wherein a bonding pattern is formed. Alternatively the bonds are accomplished by gluing or a combination of gluing and ultrasonic welding or thermobonding.

It has been an established opinion that it is the total amount of polymeric materials in the seam, for example ultrasonic weld seam, that contributes to the bond strength. Thus the bond strength would be determined only by the basis weight of the elastic laminate materials in the seam and optional additional materials added in the seam area.

According to the present disclosure this accepted opinion is contradicted, since it is shown that the relationship between the basis weights of the inner and outer nonwoven layers 22 and 23 in the elastic laminate affects the bond strength in the seam. The example presented below shows that by having a non-uniform basis weight of the first and second nonwoven layers 22 and 23, so that when the first nonwoven layer 22 forming the inner layer facing the inner layer of the other elastic laminate in the seam, has a higher basis weight than the outer second nonwoven layer 23, the bond strength will be higher than by having a uniform basis weight of the first and second nonwoven layers 22 and 23, although the total basis weight being the same.

The first and second nonwoven layers 22 and 23 may be of the same type of nonwoven materials and only differ by their basis weights.

The first nonwoven layer 22 forming the inner layer may have a basis weight in the range 13 and 30 g/m$^2$, preferably at least 15 g/m$^2$ and more preferably at least 18 g/m$^2$ and is between 10 and 300% higher than the basis weight of the second fibrous layer 23 forming the outer layer of the elastic laminate. Preferably the basis weight of the first nonwoven layer is at least 20% and more preferably at least 25% higher than the basis weight of the second nonwoven layer. The second nonwoven layer 23 may have a basis weight in the range 10 and 27 g/m$^2$.

The basis weight of the first and second nonwoven layers 22 and 23 refers to the basis weight of the original nonwoven materials used for producing the elastic laminate and not to the basis weight that the nonwoven layers may have in the elastic laminate, after having been exerted to bonding to the elastic film and other process steps during the production of the elastic laminate. For a stretch-bonded elastic laminate the nonwoven layers will contract when the stretched film is relaxed and will therefore have a higher basis weight than the original nonwoven materials.

Thus a higher bond strength in the seam area can be obtained for an elastic laminate having a given basis weight simply by choosing nonwoven layers forming the inner and outer layers of the laminate having different basis weights in the manner described above. The total basis weight of the elastic laminate remains the same and accordingly the material costs.

The basis weight of the elastic film also refers to the basis weight of the original elastic film used for producing the elastic laminate and not to the basis weight that the elastic film may have in the elastic laminate, after having been exerted to stretching and bonding to the nonwoven layers and other process steps during the production of the elastic laminate.

EXAMPLE

Two elastic laminates having a total basis weight of 58 g/m$^2$ were tested: Laminates A and B having the following material setup:

Laminate A: nonwoven 18 g/m$^2$+elastic film 22 g/m$^2$+nonwoven 18 g/m$^2$.

Laminate B: nonwoven 20 g/m$^2$+elastic film 22 g/m$^2$+nonwoven 16 g/m$^2$.

The nonwoven layers were spunbond nonwoven webs of polypropylene (PP) and the elastic film was a thermoplastic polyurethane film. Each side of the film had a nonwoven layer ultrasonically laminated to the surface. The elastic laminate was of the type stretch-bonded wherein the elastic film having an original basis weight in unstretched state of 22 g/m$^2$ was stretched about 180% and bonded to nonwoven layers having the basis weights referred to above.

Laminate A had a uniform basis weight of the two nonwoven layers on either side of the elastic film, while laminate B had a non-uniform basis weight of the two nonwoven layers. In the test the two elastic laminates of the same kind were ultrasonically welded together as in a side seam in a pant article and as illustrated in FIG. 2. For laminate A (uniform laminate) two nonwoven layers having the same basis weight, i.e. 18 g/m$^2$, were facing inwards towards each other in the seam. For laminate B (non-uniform laminate) two types of seams were made, wherein in the first seam the nonwoven layers having the lower basis weight of 16 g/m$^2$ were facing inwards towards each other in the seam and in the second seam the nonwoven layers having the higher basis weight of 20 g/m$^2$ were facing inwards towards each other in the seam.

The ultrasonic energy used in the welding was the same for all seams.

The forces needed for delaminating the side seams were measured according to the Sealing strength test described below.

The following results were obtained.
Laminate A (uniform): 19.5 N/25 mm
Laminate B (non-uniform with 16 g/m2 nonwovens facing inwards): 17 N/25 mm.
Laminate B (non-uniform with 20 g/m2 facing inwards): 20.5 N/25 mm.

Surprisingly the side seam strengths are not the same for the three samples, although the overall amount of polymeric material in the weld seams is the same. The seam of the non-uniform laminate having the nonwoven layers with the higher basis weight facing each other in the seam was stronger than the seam of the uniform laminate and for the non-uniform laminate having the nonwoven layers with the lower basis weight facing each other in the seam.

Sealing Test

The method measures the sealing strength between two materials joined together by e g gluing, welding or thermobonding.

With reference to FIG. 3 a sample strip 25 is prepared comprising a seam 26 joining two material webs 27, 28 together, wherein the seam 26 protrudes out from the plane of the sample strip 25 at a central position thereof. The width of the sample is 25 mm and the length 70 mm. A tensile tester is used having a pair of clamps 29 with a width of 25 mm and distance between the clamps of 50 mm. The sample strip 25 is fastened in the tensile tester with the transverse ends of the strip in the respective clamp. The sample strip 25 is arranged so that the seam 26 makes an angle of 90° with the strip as illustrated in FIG. 3.

Pulling is started with a crosshead speed of 300 mm/min and the pulling is stopped when the material webs 27 and 28 have separated along the seam 26.

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:
  Crosshead speed: 500 mm/min
  Clamp distance: 50 mm
  Preload: 0.05 N The sample is placed in the clamps according to the marks and it is made sure that the sample is centred and fastened perpendicularly in the clamps. The tensile tester is started and three cycles between 0 and the predetermined elongation are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

A non-elastic material is defined as a material having a permanent elongation after relaxation of more than 10% after having been subjected to an elongation of 30%.

The invention claimed is:

1. A pant-type absorbent article comprising a front portion, a back portion and a crotch portion, wherein lateral side portions of the front portion and back portion are superposed so that their inner surfaces face each other and are joined to each other along side seams to define a waist opening and a pair of leg openings of said pant-type article, and wherein at least part of, including said lateral side portions, of said front portion and said back portion comprises an elastic laminate, said elastic laminate comprising first and second fibrous layers and an elastic film layer located there between, wherein said first fibrous layer of said elastic laminate forming the inner wearer-facing side of the elastic laminate has a basis weight of between 13 and 30 g/m2 and wherein the basis weight of the first fibrous layer is between 10 and 300% higher than the basis weight of the second fibrous layer of the elastic laminate, wherein the first fibrous layers face each other along said side seams.

2. A pant-type absorbent article as claimed in claim 1, wherein said side seams are provided by ultrasonic welding, or thermal bonding or glue or by combinations thereof.

3. A pant-type absorbent article as claimed in claim 1, wherein said first fibrous layer is a nonwoven material selected from the following group: spunbond, meltblown, carded, hydroentangled, spunbond-meltblown-spunbond (SMS), and spunbond-meltblown (SM).

4. A pant-type absorbent article as claimed in claim 3, wherein said second fibrous layer is a nonwoven material selected from the following group: spunbond, meltblown, hydroentangled, carded, spunbond-meltblown-spunbond (SMS), and spunbond-meltblown (SM).

5. A pant-type absorbent article as claimed in claim 1, wherein said first and second fibrous layers are of the same type of fibrous material and differ only by their basis weights.

6. A pant-type absorbent article as claimed in claim 1, wherein the elastic laminate extends transversely across the width of the front portion as well as transversely across the width of the back portion.

7. A pant-type absorbent article as claimed in claim 1, wherein said first fibrous layer of said elastic laminate forming the inner wearer-facing side of the elastic laminate has a basis weight of at least 15 g/m$^2$.

8. A pant-type absorbent article as claimed in claim 1, wherein the basis weight of the first fibrous layer is at least 20% higher than the basis weight of the second fibrous layer of the elastic laminate.

9. A pant-type absorbent article as claimed in claim 8, wherein the basis weight of the first fibrous layer is not more than 200% higher than the basis weight of the second fibrous layer of the elastic laminate.

10. A pant-type absorbent article as claimed in claim 1, wherein the elastic laminate is a stretch-bonded laminate.

11. A pant-type absorbent article as claimed in claim 1, wherein said first fibrous layer of said elastic laminate forming the inner wearer-facing side of the elastic laminate has a basis weight of at least 18 g/m$^2$.

12. A pant-type absorbent article as claimed in claim 1, wherein the basis weight of the first fibrous layer is at least 25% higher than the basis weight of the second fibrous layer of the elastic laminate.

\* \* \* \* \*